United States Patent [19]

England et al.

[11] B 4,001,319
[45] Jan. 4, 1977

[54] PROCESS FOR THE PREPARATION OF CARBACYL HALOSULFATES

[75] Inventors: David C. England; Carl G. Krespan, both of Wilmington, Del.

[73] Assignee: E. I. Du Pont de Nemours and Company, Wilmington, Del.

[22] Filed: May 7, 1973

[21] Appl. No.: 357,526

[44] Published under the second Trial Voluntary Protest Program on March 23, 1976 as document No. B 357,526.

[52] U.S. Cl. .......................... 260/545 R; 260/2 D; 260/400

[51] Int. Cl.$^2$ ...................... C07F 143/70

[58] Field of Search ................. 260/545 R, 400

[56] References Cited

UNITED STATES PATENTS

| | | | |
|---|---|---|---|
| 2,273,974 | 2/1942 | Meiser | 260/507 R |
| 2,628,253 | 2/1953 | Dowdall | 260/545 R |
| 3,102,139 | 8/1963 | Lawlar et al. | 260/546 |
| 3,214,443 | 10/1965 | Chiang et al. | 260/327 |
| 3,351,644 | 11/1967 | Hauptschein et al. | 260/544 F |
| 3,493,611 | 2/1970 | Sweeney | 260/544 F |

OTHER PUBLICATIONS

Paul et al., "Indian J. Chem.," 10 (1), (Jan. 1972), pp. 92–93.
Paul et al., "Z. Anorg. Allg. Chem.," Band 321, (1963), pp. 62–69.
Belaventseu et al., Zh. Organ. Khim., 9 (2), pp. 256–259, (Feb., 1973).

Primary Examiner—Lorraine A. Weinberger
Assistant Examiner—Michael Shippen

[57] ABSTRACT

Compounds containing carboxylic acid fluoride or chloride groups react with sulfur trioxide at temperatures between −30° to about 100° C to give carbonyl fluoro- or chlorosulfates. Preferred reactants are polyfluoroalkyl or polyfluoroalkenyl carbacyl acid fluorides. The carbacyl halosulfates are useful as cationic polymerization catalysts and as chemical intermediates.

1 Claim, No Drawings

PROCESS FOR THE PREPARATION OF CARBACYL HALOSULFATES

FIELD OF THE INVENTION

This invention relates to a method of making carbacyl halosulfates.

THE PRIOR ART

Certain perhalocarbacyl fluorosulfates,

are known, as shown in the following tabulation.

| Reference | $R_f$ |
|---|---|
| 1. Des Marteau and Cady, Inorg. Chem. 5, 169 (1966); Chem. Abs. 64, 8020 (1966) | Trifluoromethyl Chlorodifluoromethyl Pentafluoroethyl Heptafluoropropyl 2-(Fluorosulfonyloxy)-tetrafluoroethyl |
| 2. Delfino and Shreeve, Inorg. Chem. 5, 308 (1966); Chem. Abs. 64, 12544 (1966) | Trifluoromethyl |
| 3. Fox & Franz, Inorg. Chem. 5, 946 (1966); Chem. Abs. 65, 1750 (1966) | Fluoro |
| 4. Mishri & Shreeve, J. Am. Chem. Soc. 90, 1711 (1968); Chem. Abs. 69, 26685 (1968) | Heptafluoroisopropyl α-(Fluorosulfonyloxy)-hexafluoroisopropyl |

These fluorosulfates are described as being formed by reaction of peroxydisulfuryl difluoride with appropriate perhalocarboxylic acid anhydrides (Ref. 1), with trifluoroacetyl bromide (Ref. 2) and with bis(trifluoromethyl)ketene (Ref. 4); by reaction of fluorine fluorosulfate with bis(trifluoromethyl)ketene (Ref. 4); and by photolysis of bis(monofluorocarbonyl)peroxide in the presence of sulfur dioxide (Ref. 3).

Acetyl chlorosulfate,

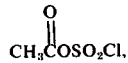

formed by reaction of acetyl chloride and chlorosulfonic acid at room temperature, is described as a "transient" product which rearranged to sulfoacetyl chloride,

above 45° (Huntress, "Organic Chlorine Compounds", Wiley, New York, N.Y., 1948).

The reaction of aromatic acid chlorides (e.g., benzoyl, 2-toluyl and 4-chlorobenzoyl chlorides) with sulfur trioxide at 110°–160° has been reported [Gilbert, Chem. Rev. 62, 575 (1962)], with the result illustrated below:

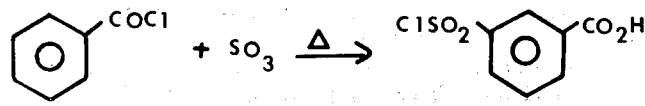

Other art describes the reaction of perfluoroalkyl iodides with sulfur trioxide in the presence of a pentavalent antimony halide to form perfluoroalkane-carbacyl fluorides,

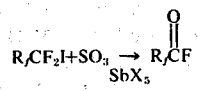

(Sweeney and Yao, U.S. Pat. No. 3,493,611); and the reaction of sulfur trioxide with alkyl polyhaloalkyl ethers at −30° to +20° to give polyhaloacyl fluorides and alkyl fluorosulfates,

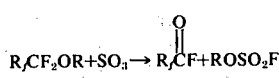

[Belaventsev et al., U.S.S.R. 251,567; Chem. Abs. 72, 42819 (1970)].

SUMMARY OF THE INVENTION

The present invention is a method of making carbacyl halosulfates wherein halogen is fluorine or chlorine by contacting and reacting an organic compound containing at least one carbacyl halide group with sulfur trioxide at a temperature in the range between −30°C and 100°C.

The reaction can be expressed by the equation

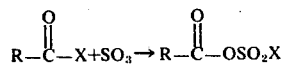

wherein $X$ is chlorine or fluorine.

Provided R is not attacked by $SO_3$, the products will correspond to the starting materials as illustrated in the above equation.

Preferred R groups in the above equation have up to 22 carbon atoms and are alkyl, haloalkyl, including polyhaloalkyl (halo = $X$), halosulfonylalkyl (halo = $X$), halosulfonylhaloalkyl (halo = $X$), polyhaloalkenyl (halo = $X$), polyfluoroalkyl containing α-difluoromethyleneoxy ($-CF_2O-$) groups, phenyl or phenyl substituted with one or more of

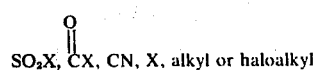

(halo = $X$).

A preferred process involves the foregoing reactants wherein X is fluorine and R is polyfluoroalkyl or polyfluoroalkenyl of up to 22 carbon atoms.

DETAILED DESCRIPTION OF THE INVENTION

The process is suitably carried out by admixing the sulfur trioxide and carbacyl halide reactants under appropriate conditions in an anhydrous system and allowing the reaction to proceed spontaneously, the mixing being done with caution in view of possible exothermic reaction. The temperature can be in the range from about −30° to about +100° and is usually established at a level where reaction proceeds at a practical rate. The pressure is not critical, being generally atmospheric pressure or above depending upon whether a vented or sealed reactor is used. The reaction time is likewise not critical and can be from a very short (∼1 minute) to a relatively long (∼ several weeks) period, practical times being dependent upon the reaction rate under the conditions employed.

The reaction can be carried out "neat", i.e., without any added material, or an inert diluent or solvent can be used if desired. Added materials should be resistant to attack by sulfur trioxide, e.g., inert solvents such as chlorinated aliphatic compounds (methylene chloride, 1,2-dichloroethane, tetrachloroethylene) and fluorinated aliphatic compounds (1,2-dichloro-1,1,2,2-tetrafluoroethane, perfluoroethers).

Ordinarily the sulfur trioxide and carbacyl halide reactants are used in equimolar amounts, although the mol ratio is not critical. However, when a carbacyl halide reactant also contains an alkyl-OCF$_2$-group, this group can be converted to a carbonyl fluoride group, as follows:

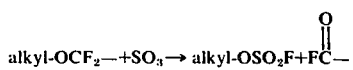

alkyl-OCF$_2$—+SO$_3$→ alkyl-OSO$_2$F+FC—

(cf. Belaventsev et al., U.S.S.R. 251,567; England, U.S. Pat. No. 3,641,142). In this instance, since the product moiety containing the carbonyl fluoride group can react further with sulfur trioxide by the process of the invention, the mol ratio of sulfur trioxide to original alkyl-OCF$_2$-containing carbacyl halide can be at least 3 to 1 without being an excessive mol ratio.

It should be pointed out that in view of the above-indicated reaction of alkyl-OCF$_2$-containing compounds with sulfur trioxide, the hitherto unrecognized process of the invention can be considered operative in any such reaction mixture, particularly when the mol ratio of sulfur trioxide to each alkyl-OCF$_2$-moiety is more than 1:1.

The following examples illustrate the process of the invention. In these examples temperatures are given in degrees centigrade.

EXAMPLE 1

Trifluoroacetyl Fluorosulfate

A. Preparation of Trifluoromethyl Fluorosulfate

Into each of two 100-ml heavy-walled glass polymer tubes was loaded 20 g (0.25 mol) of sulfur trioxide and 32.5 g (0.28 mol) of trifluoroacetyl fluoride. The tubes were sealed and allowed to stand at 25° for 3 weeks, after which time single phases were present. Excess trifluoroacetyl fluoride was allowed to escape and the combined contents of both tubes was distilled to give 67.4 g (69%) of colorless product, bp 44°–47° (lit bp 47°); nmr (CCl$_4$): $^{19}$F+47.7 (1, singlet, —OSO$_2$F) and −74.5 ppm (3, singlet, CF$_3$).

B. Polymerization of Tetrahydrofuran with Trifluoroacetyl Fluorosulfate

Into a flame-dried round-bottomed flask was injected 44.4 g (50 ml) of purified tetrahydrofuran. The contents were blanketed with dry nitrogen and stirred at −25° while 0.10 ml of trifluoroacetyl fluorosulfate was injected. Stirring was continued while the mixture was allowed to warm to 25°. After one day the mixture was too viscous to be stirred magnetically. After two days, the polymerization was quenched in 250 ml of water containing 10 g of sodium hydroxide. This mixture was warmed and stirred for one hour, and the resulting semisolid polymer was washed with three 250-ml portions of hot water, then dried under vacuum to give 32.7 g (74%) of solid polytetrahydrofuran, $\eta_{inh}$ = 0.80 (0.1% solution in benzene at 25°).

EXAMPLE 2

α-H-Tetrafluoropropionyl Fluorosulfate

A heavy-walled sealed glass tube containing 37 g (0.25 mol) of α-H-tetrafluoropropionyl fluoride and 10 ml (ca 0.25 mol) of sulfur trioxide was heated in a steam bath overnight. The contents of the tube was then fractionally distilled, yielding α-H-tetrafluoropropionyl fluorosulfate as a main fraction, 36.1 g, bp 49°(65 mm). A portion was redistilled at atmospheric pressure, bp 75°–77°.

Anal. Calcd for C$_3$HF$_5$O$_4$S: C, 15.80; H, 0.44; F, 41.67; S, 14.06. Found: C, 15.86; H, 0.60; F, 41.57; S, 14.07.

EXAMPLE 3

α-H-Hexafluoroisobutyryl Fluorosulfate

Addition of 50 g (0.25 mol) of α-H-hexafluoroisobutyryl fluoride to 24 g (0.30 mol) of sulfur trioxide resulted in a mildly exothermic initial reaction. After two days at room temperature the mixture was distilled to afford 48.2 g (69%) of α-H-hexafluoroisobutyryl fluorosulfate, bp 49° (50 mm). Ir: 3.37 (satd CH, weak), 5.47 (C=O), 6.76 (SO$_2$F), and 7.2–8.5 μ (CF, SO$_2$). Nmr (CCl$_4$): H, 4.22 ppm (septet, J$_{HF}$ 7 Hz, CH(CF$_3$)$_2$); $^{19}$F + 46.6 (1, singlet, OSO$_2$F), −64.6 ppm (6, doublet, CH(CF$_3$)$_2$).

Anal. Calcd for C$_4$HF$_7$O$_4$S: C, 17.27; H, 0.36; F, 47.82. Found: C, 17.61; H, 0.69; F, 48.53.

EXAMPLE 4

Perfluoromethacrylyl Fluorosulfate

A. Preparation of Perfluoromethacrylyl Fluorosulfate

Equimolar amounts of perfluoromethacrylyl fluoride (U.S. Pat. No. 3,362,990) and sulfur trioxide gave a mildly exothermic reaction when mixed at room temperature. Attempted distillation of the reaction mixture at 125°–140° and atmospheric pressure resulted in dissociation, presumably to starting materials, bp ∼49°.

A 10 g sample of the distillate above, bp ∼49° (1 atm), was distilled under reduced pressure to give 7.5 g of perfluoromethacrylyl fluorosulfate, bp 46°–48° (20 mm). Ir: 5.53 (C=O), 5.91 (C=C), 6.79 (SO$_2$F), and 7.2 to 8.5 μ (CF, SO$_2$). Nmr: $^{19}$F + 45.0 (1, singlet, OSO$_2$F), −47.7 (2, multiplet, =CF$_2$), and −60.4 ppm (3, multiplet, CF$_3$). Ir and nmr also indicated trace impurities to be present.

Anal. Calcd for C$_4$F$_6$O$_4$S: C, 18.61; F, 44.17. Found: C, 18.78; F, 44.49.

B. Reaction of Perfluoromethacrylyl Fluorosulfate with Dimethyl Ether

Excess dimethyl ether was distilled into a flask topped by a −80° condenser and containing 41.7 g (0.16 mol) of perfluoromethacrylyl fluorosulfate maintained at 0°. The mixture was stirred at 0° for one hour and then allowed to warm to 25° while excess dimethyl ether was vented. The residual product was passed over a bed of dry sodium fluoride pellets in hot tube at 275° (5 mm pressure). After two passes, only traces of by-product methyl fuorosulfate remained and nearly pure methyl perfluoromethacrylate was collected in 79% (23.9 g) yield. Identity and purity of the methyl perfluoromethacrylate were determined by comparison of the ir spectrum with that of an authentic sample.

EXAMPLE 5

α-(Fluorosulfonyl)tetrafluoropropionyl Fluorosulfate

A heavy-walled sealed glass tube containing 46 g (0.2 mol) of α-(fluorosulfonyl)tetrafluoropropionyl fluoride and 16 g (0.2 mol) of sulfur trioxide was heated in a steam bath overnight. The reaction product was distilled under reduced pressure to yield 9.6 g of α-(fluorosulfonyl)tetrafluoropropionyl fluorosulfate, bp 71°(192 mm). Ir: 5.40 (C=O), 6.66 ($SO_2F$) and 6.76 μ ($SO_2F$). Nmr: $^{19}F$ +47.0 (1, singlet, $OSO_2\underline{F}$), +52.1 (1, singlet, $SO_2\underline{F}$), −74.1 (3, multiplet, $C\underline{F}_3$), −161.6 ppm (1, singlet, =C$\underline{F}$).

EXAMPLE 6 m-Trifluoromethylbenzoyl Fluorosulfate

Addition of 7.5 g (0.094 mol) of sulfur trioxide over a 10-minute period to 19.2 g (0.10 mol) of m-trifluoromethylbenzoyl fluoride proceeded exothermically. Temperature was maintained at 30°–40° by external cooling. After addition was complete, infrared analysis of the mixture showed strong bands at 5.49 μ (C=O) and 6.84 μ (—$OSO_2F$). Distillation at 42°–47° (0.15–0.25 mm) afforded 14.2 g of liquid. Nmr analysis of a late fraction by $^{19}F$ nmr showed peaks at +45.3 ppm (singlet, 1, —$OSO_2\underline{F}$) and −64.1 ppm (singlet, 3, C$\underline{F}_3$) with a —COF peak present to a point indicating ~9% starting acid fluoride as impurity. The product is very reactive as indicated by rapid deposition of solid on contact with moist air. Ir (with $CaF_2$ plates): 3.23 (aromatic CH), 5.48 (C=O), 6.18 and 6.27 (aromatic C=C), and 6.84 μ ($OSO_2F$).

EXAMPLE 7

Heptafluorobutyryl Chlorosulfate

Reaction of equimolar amounts of heptafluorobutyryl chloride and sulfur trioxide at 25° did not proceed satisfactorily, as indicated by the continued presence of two phases after 3 days. The two reactants, when heated in a sealed glass tube at 100° for 2 hrs, formed a homogeneous solution. After an additional 2 hrs at 100°, the reaction mixture was cooled and transferred to a still. Distillation of about 1/5 of the mixture occurred readily at 33°–34° with the pot at ~50° at atmospheric pressure. Ir analysis of the distillate indicated it to contain a high proportion of heptafluorobutyryl chloride (bp 39°); and the corrosive, fuming nature of the distillate indicated $SO_3$ or a derivative of it to be present in at least small amount.

Ir analysis of the still pot contents showed it to contain not only heptafluorobutyryl chloride (5.51 and 5.58 μ for C=O), but also heptafluorobutyryl chlorosulfate 85.46 μ for C=O, 7.10 μ for $OSO_2Cl$).

EXAMPLE 8

Benzoyl Chlorosulfate

Benzoyl chloride (14.1 g, 0.10 mol) was stirred under dry nitrogen while 8.0 g (0.10 mol) of sulfur trioxide was added over 10 minutes with occasional cooling to keep the temperature at 30°–40°. After the addition was completed, the mixture was allowed to stand one hour, then distilled through a short Vigreux column to give 21.9 g (99%) of yellow oil, bp 37° (7.5 μ). Nmr for $^1H$ showed monosubstituted phenyl, nearly unchanged in chemical shift and in pattern from that of benzoyl chloride. Ir showed strong bands at 5.57 (C=O), 6.27 and 6.32 (aromatic C=C), and 7.07 μ ($OSO_2Cl$).

Utility

The carbacyl halosulfates obtainable by the process of this invention react electrophilically with aliphatic ethers. Accordingly, they are useful as cationic catalysts for the polymerization of tetrahydrofuran, as demonstrated in part B of Example 1.

Further the electrophilic reaction with ethers also provides a new synthetic method useful for the preparation of certain esters, e.g., the preparation of methyl perfluoromethacrylate from perfluoromethacrylyl fluorosulfate and dimethyl ether as described in Part B of Example 4. Methyl perfluoromethacrylate is difficult to obtain by conventional means.

Since obvious modifications and equivalents in the invention will be evident to those skilled in the art, we propose to be bound solely by the appended claims.

The embodiments of the invention in which an exclusive property or privilege is claimed are defined as follows:

1. Method of making carbacyl fluorosulfates which comprises contacting and reacting trifluoroacetyl fluoride with sulfur trioxide at −30°C to 100°C.

* * * * *

UNITED STATES PATENT OFFICE
CERTIFICATE OF CORRECTION

PATENT NO. : 4,001,319
DATED : JANUARY 4, 1977
INVENTOR(S) : DAVID C. ENGLAND & CARL G. KRESPAN

It is certified that error appears in the above-identified patent and that said Letters Patent are hereby corrected as shown below:

Column 6, line 13, "85.46" should be -- 5.46 --.

Signed and Sealed this

Third Day of May 1977

[SEAL]

Attest:

RUTH C. MASON
*Attesting Officer*

C. MARSHALL DANN
*Commissioner of Patents and Trademarks*